(12) United States Patent
Canpolat et al.

(10) Patent No.: US 6,660,995 B1
(45) Date of Patent: Dec. 9, 2003

(54) PARTICLE SIZE ANALYSIS IN A TURBID MEDIA WITH A SINGLE-FIBER, OPTICAL PROBE WHILE USING A VISIBLE SPECTROMETER

(75) Inventors: Murat Canpolat, Plantation, FL (US); Judith R. Mourant, White Rock, NM (US)

(73) Assignee: Regents of the University of California, Oakland, CA (US)

( * ) Notice: Subject to any disclaimer, the term of this patent is extended or adjusted under 35 U.S.C. 154(b) by 241 days.

(21) Appl. No.: 09/888,799

(22) Filed: Jun. 25, 2001

(51) Int. Cl.[7] .......................... G01N 21/85; G01N 21/25

(52) U.S. Cl. .................... 250/227.23; 250/574; 356/39; 356/336

(58) Field of Search ................... 250/227.11, 227.18, 250/227.23, 573, 574, 226, 222.2; 356/39, 40, 41, 42, 335, 336, 337, 338; 600/310, 322, 476

(56) References Cited

U.S. PATENT DOCUMENTS

| | | | |
|---|---|---|---|
| 4,497,577 A | 2/1985 | Sato et al. | 383/186 |
| 4,940,326 A | 7/1990 | Tatsuno | 356/336 |
| 5,610,712 A | 3/1997 | Schmitz et al. | 356/335 |
| 5,687,730 A | 11/1997 | Doiron et al. | 128/665 |
| 6,526,299 B2 * | 2/2003 | Pickard | 600/310 |
| 2002/0135752 A1 * | 9/2002 | Sokolov et al. | 356/39 |

* cited by examiner

*Primary Examiner*—Kevin Pyo
(74) *Attorney, Agent, or Firm*—Madson & Metcalf

(57) ABSTRACT

Apparatus and method for measuring scatterer size in a dense media with only a single fiber for both light delivery and collection are disclosed. White light is used as a source and oscillations of the detected light intensities are measured as a function of wavelength. The maximum and minimum of the oscillations can be used to determine scatterer size for monodisperse distributions of spheres when the refractive indices are known. In addition several properties of the probe relevant to tissue diagnosis are disclosed including the effects of absorption, a broad distribution of scatterers, and the depth probed.

23 Claims, 16 Drawing Sheets

PARTICLE SIZE ANALYSIS IN A TURBID MEDIA WITH A SINGLE-FIBER, OPTICAL PROBE WHILE USING A VISIBLE SPECTROMETER

GOVERNMENT RIGHTS

This invention was made with Government support under Contract Number W-7405-ENG-36 awarded by the United States Department of Energy to The Regents of the University of California. The Government has certain rights in the invention.

BACKGROUND OF THE INVENTION

Technical Field

The present invention is drawn to an apparatus and method for analyzing particle size in a dense suspension using a single fiber optical probe with a light spectrometer.

BACKGROUND OF THE INVENTION

In situ measurement of particle size in turbid media has many applications in medicine and in the pharmacology industry. Many diseases are correlated with the morphological alterations of cells, which are used for diagnosis in pathology. An inexpensive, non-invasive, in-vivo technique to detect alterations of scatterer size in tissue would improve patient care and reduce medical cost.

Known methods of measuring particle-size in dense suspensions include frequency-domain photon migration and other photon diffusion based techniques that measure the wavelength dependence of the reduced scattering coefficient. An average effective scatterer size can be determined from a simple parameterization of the wavelength dependence of $\mu_s'(\lambda)$. Alternatively, the size distribution and volume ratio of particles can be calculated from $\mu_s'(\lambda)$ using an inversion method. The disadvantage of photon diffusion based techniques is that the volume sampled must be large enough for the diffusion approximation to hold, i.e.~1 cm$^3$ or larger. A smaller volume is probed, ~3 mm$^3$, when variations in the pattern of polarized light back-scattered from a turbid media are used to estimate scatter size. However, this method does not provide information on the scatterer size distribution width. Backman et al. have recently reported using polarized diffuse reflectance spectroscopy to determine scatterer size distributions. V. Backman et al., "Polarized light scattering spectroscopy for quantitative measurement of epithelial cellular structures in situ," IEEE J. Sel. Top. Q. Electronics, vol. 5, pp. 1019–26, (1999). Scatterer size distributions can be determined from non-polarized wavelength dependent diffuse reflectance measurements when the measurement wavelength is much less than the scatterer diameter. Additional methods of particle size distribution determination based on the anomalous diffraction approximation are currently being developed.

From the foregoing, it will be appreciated that there is a need in the art for an inexpensive, in situ technique to detect alterations of scatterer size in tissue, turbid, or dense media.

SUMMARY OF THE INVENTION

The present invention is drawn to an in situ technique to determine scatterer size by measuring the white light elastic scattering spectroscopy (ESS) signal with a single-fiber, optical probe. The single-fiber, optical probe is optically coupled to a light source and optically coupled to a spectrometer. In this way, the probe serves to introduce light into the sample and to collect light scattered by the sample. The collected light is transmitted to the spectrometer. An elastic scatter signal (ESS) spectrum of the sample is measured and analyzed to determine the scatterer particle size. The particle size analysis method may include compensating for the refractive index and/or light absorption of the sample medium.

It has been observed that different size particles have distinct oscillation patterns in an ESS spectrum. Furthermore, the frequency of oscillations increases with particle size, and the particle size is approximately a linear function of the total number of oscillations. Derivatives of the spectra with respect to wavelength make the oscillation pattern easier to count. Thus, particle size is related to the number of oscillations in a given wavelength range. The spectra wavelength may range from 100 to 900 nm, more preferably from 450 to 800 nm.

The use of a single fiber probe of small diameter has several advantages. A fairly small volume is probed allowing for local measurement of particle size. Secondly, the probe can easily fit and into small compartments in an industrial setting and down endoscope channels for performing tissue spectroscopy. The experimental setup incorporating the fiber optic probe is simple and inexpensive, requiring only one steady-state visible-NIR spectrometer.

DETAILED DESCRIPTION OF THE INVENTION

Figure 1:
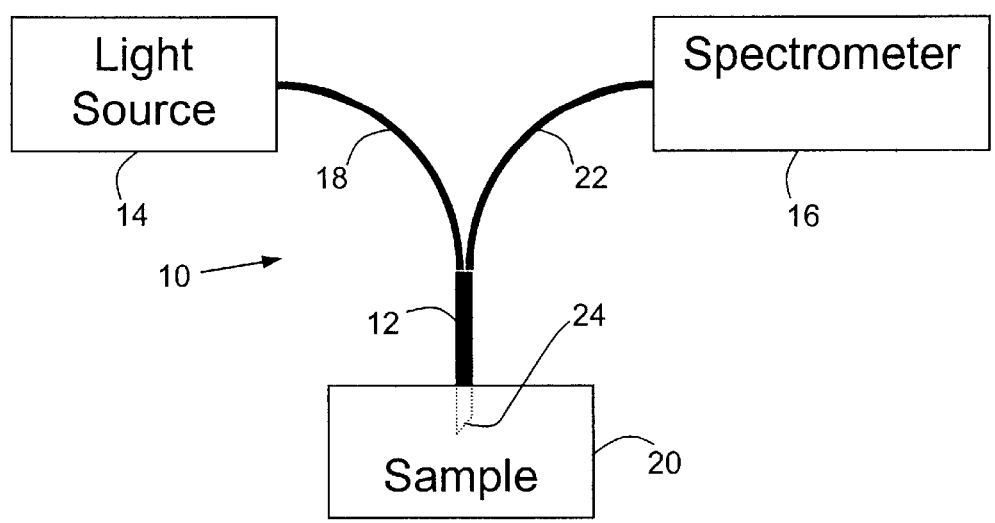
FIG. 1 is a representation of the typical apparatus used in the Examples and Monte Carlo simulations.

The present invention is drawn to in situ particle size analysis using a single fiber, optical probe. According to the technique, scatterer size is determined from oscillations observed in the elastic scattering spectroscopy (ESS) signal. The oscillation frequency increases with particle size, and the particle size is approximately a linear function of the total number of oscillations over a given wavelength range. Therefore, knowing the number of oscillations, one can determine the particle size. Furthermore, as discussed in greater detail below, particle size analysis is generally independent of the particle concentration. Also, absorption has very little affect on the particle size analysis.

The single-fiber, optical probe is preferably optically coupled to a light source and optically coupled to a spectrometer. Thus, the probe serves both to introduce light into the sample and to collect light scattered by the sample. The collected light is transmitted to the spectrometer. The spectrometer is selected to provide the desired wavelength range. In this case, the spectra wavelength preferably ranges from about 100 to 900 nm, and more preferably from 450 to 800 nm. A high throughput spectrometer is preferred to help reduce the signal to noise of the overall system. An elastic scatter signal (ESS) spectrum of the sample is measured and analyzed to determine the scatterer particle size. The particle size analysis method may include compensating for the refractive index and/or light absorption of the sample medium.

The single fiber optical probe is manufactured of a light-transmitting material, such as quartz. The single fiber optical probe preferably has a diameter in the range from 50 μm to 600 μm and more preferably from 100 μm to 300 μm. A diameter of about 200 μm is particularly preferred. The optical probe preferably has a numerical aperture less than 0.3, and more preferably 0.22 or less.

One potential problem of using the same fiber probe to collect scattered light that is used to deliver light is the tendency for specular reflection of the light, which can interfere with the scattered light signal. The optical probe tip is preferably structurally modified to inhibit specular reflection of the light. For example, the tip may be polished at an angle sufficient to inhibit specular reflection of the light. Typical angle ranges from 45 to 55 degrees. The preferred angle will vary depending on the numerical aperture of the fiber probe. The probe tip may also contain an antireflection coating to inhibit specular reflection. Alternatively, the probe or spectrometer may include one or more filters to block the reflected light.

The use of a single fiber probe of small diameter has several advantages. A fairly small volume is probed allowing for local measurement of particle size. Secondly, the probe can easily fit and into small compartments in an industrial setting and down endoscope channels for performing tissue spectroscopy. The experimental setup incorporating the fiber optic probe is simple and inexpensive, requiring only one steady-state visible-NIR spectrometer. Measurements can be performed on dense media with a small probe.

Apparatus. FIG. 1 shows the general configuration of the apparatus 10 used in accordance with the present invention. In the apparatus, a single fiber, optical probe 12, is optically coupled to a light source 14 and optically coupled to a spectrometer 16. In the apparatus used in the Examples, the light source 14 was a tungsten lamp (Gilway Technical lamp, L1041, Woburn, Mass.). An optical fiber 18 carries light from the light source 14 to the probe 12. The optical probe 12 is placed in a sample 20. Scattered light from the sample is collected by the optical probe 12. An optical fiber 22 carries the scattered light signal from the probe 12 to the spectrometer 16.

In the apparatus used in the Examples, the probe 12 was 200 μm in diameter and had a numerical aperture of 0.22. Optical fibers 18, 22 were 100 μm fibers butted up against the 200 μm fiber probe 12 in an SMA barrel connector. It will be appreciated that the diameter size of probe 12 and fibers 18 and 22 can vary. Currently, probe 12 has a diameter ranging from 50 μm to 600 μm, and more preferably from 100 μm to 300 μm. The design of probe 12 is similar to that of Moffit and Prahl (T. P. Moffit and S. A. Prahl, "In vivo sized fiber spectroscopy," Proceedings of SPIE, vol. 3917, pp. 2225–31 (2000)) with an important difference. To avoid specular reflection, the probe tip 24 was polished at an angle of about 50 degrees. The spectrometer used to disperse the collected light was spectrograph model 275i, Acton Research Corporation, Acton, Mass. A sensor, such as a two-dimensional, thermoelectrically-cooled CCD array, was used to measure the dispersed spectra. Spectra were collected in the wavelength range 450–900 nm.

EXAMPLES

The following examples are given to illustrate various embodiments within the scope of the present invention. These are given by way of example only, and it is to be understood that the following examples are not comprehensive or exhaustive of the many types of embodiments of the present invention that can be prepared in accordance with the present invention.

EXAMPLE 1

Ten aqueous suspensions of monodisperse polystyrene microspheres (Duke Scientific, Palo Alto, Calif.) were used in the experiments. Diameters of the microspheres were 0.194, 0.329, 0.426, 0.451, 0.505, 0.672, 0.852, 0.890, 0.990, 1.530 and 2.020 μm. All measurements were performed on suspensions with reduced scattering coefficients of 0.75 mm$^{-1}$ and 1.50 mm$^{-1}$. The spectra were corrected for the wavelength dependence of system components and a small amount of specular reflection. The corrected spectrum, $I_c$, is $$I_c = \frac{I_t - I_b}{I_x - I_b} \quad (1)$$

where, $I_t$ is a spectrum of the scattering medium, $I^s$ is a spectrum of Spectralon (Labsphere, Inc.) in water and $I_b$ is a spectrum taken of nanopure water in a flat black container. In the one case where measurements were made of polystyrene spheres in optical couplant, $I_b$ is a spectrum taken of optical couplant (Dow Coming Q2-3067, Midland, Mich.) in a flat black container. In both cases $I_b$ is a measure of the specular reflectance of the probe/medium interface.

Derivatives of the spectra with respect to wavelength were taken to make the correlation between particle size and the oscillation pattern clearer. Before taking the derivatives, the spectra were smoothed using a binomial filter. (IGOR Pro version 3.13 WaveMetrics Inc., Lake Oswego, Oreg.).

Monte Carlo modeling of photon transport was performed to investigate the depth into the scattering medium probed by the single fiber probe, and the effects of having a distribution of scatterer sizes in contrast to a monodisperse distribution. The Monte Carlo modeling code for unpolarized light does not need to keep track of the Stokes vector, the azimuthal scattering angle may be chosen from a uniform distribution, and the scattering angle, θ, can be chosen from a table. For the modeling, it was assumed that the delivery and collection fibers were identical. In contrast to the experimental work for which the probe was polished at an angle, the surface of the fiber was assumed to be parallel to the surface of the scattering medium. Photons were terminated if they reached a distance greater than 0.75 cm from the center of the probe surface.

The measurement of elastic scattering using a single fiber probe is difficult because of the specular reflection from the probe/medium interface. To decrease this problem, the optical fiber was polished at an angle of about 50° (instead of 90°). Although this greatly reduced the specular reflection, it was still necessary to subtract the specular reflection. This was accomplished by measuring the medium without scatterers present in a black container. If a single optical fiber were to be used for tissue spectroscopy, the appropriate medium would be water or water with a substance added to slightly increase the refractive index.

EXAMPLE 2

Figure 2:
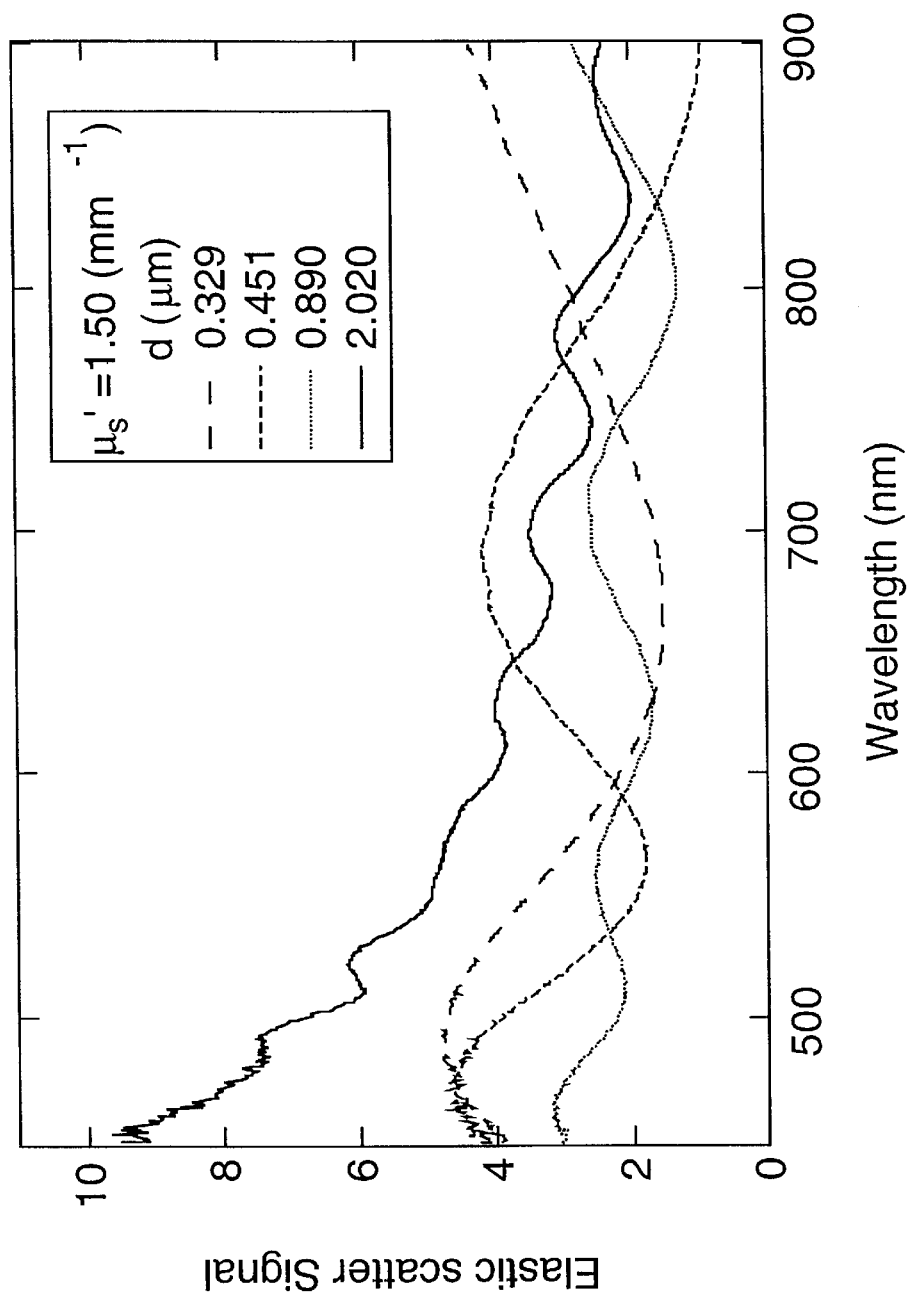
FIG. 2 is a graph of the elastic scatter spectrum of several tissue phantoms obtained using polystyrene spheres having diameters (d) of 0.329, 0.451, 0.890, and 2.020 μm. The reduced scattering coefficient, $\mu_s'=1.5$ mm$^{-1}$ at 633 nm.
Figure 3:
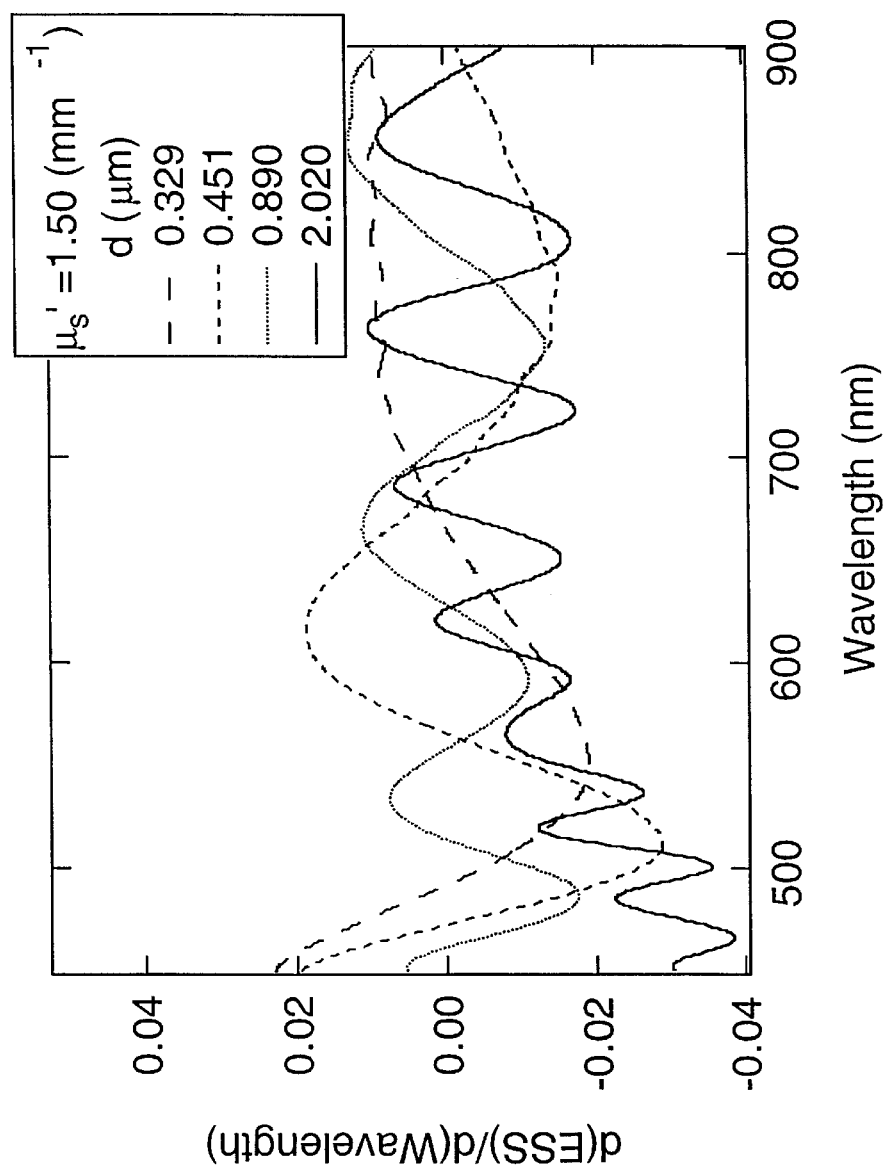
FIG. 3 is graph of the derivatives of the spectra of FIG. 2.
Figure 4:
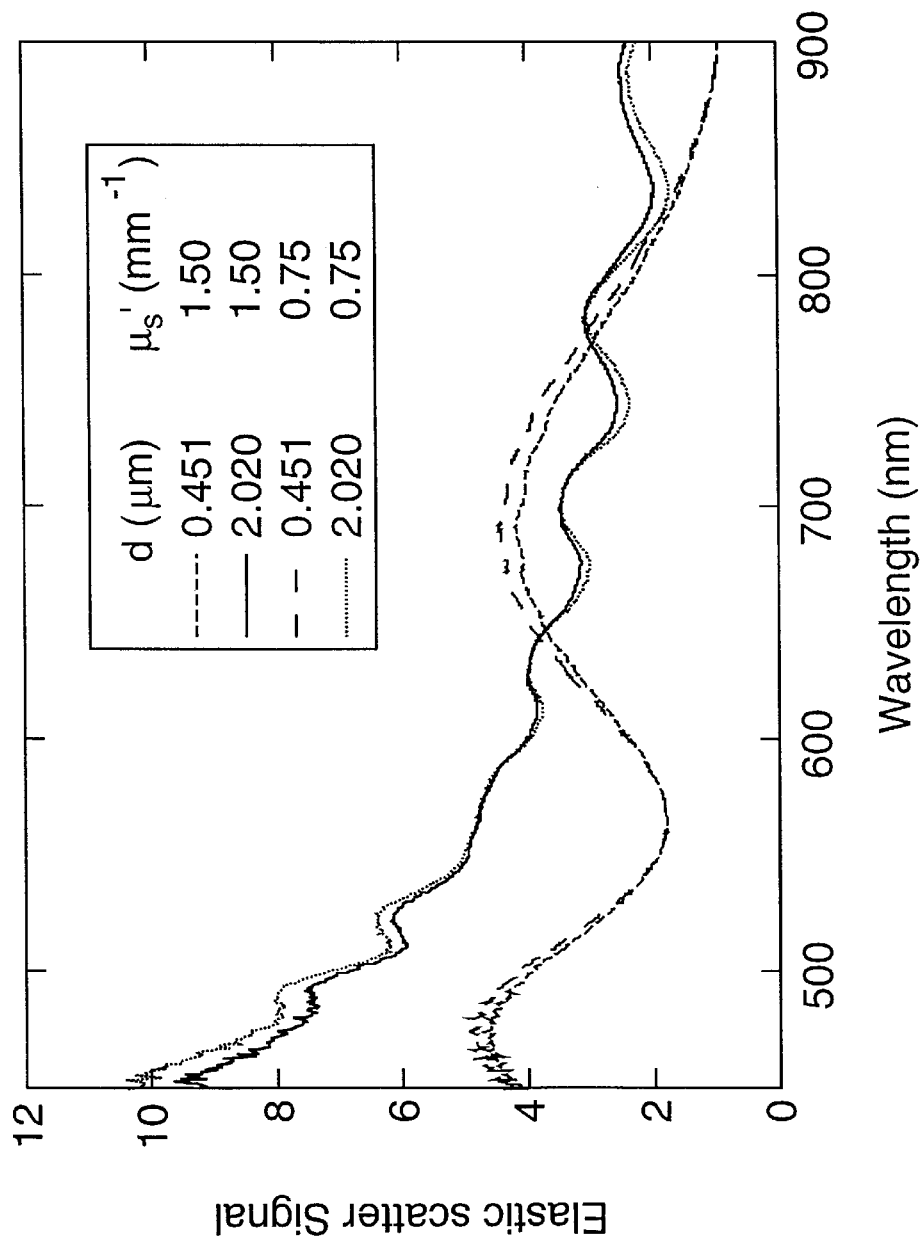
FIG. 4 is the graph of the elastic scatter spectra for two reduced scattering coefficients, $\mu_s'=0.75$ mm$^{-1}$ and $\mu_s'=1.50$ mm$^{-1}$, for two different particle sizes, 0.451 and 2.020 μm. Spectra of the same size spheres have been scaled to have the same amplitude in order to facilitate comparison of wavelength dependent differences.
Figure 5:
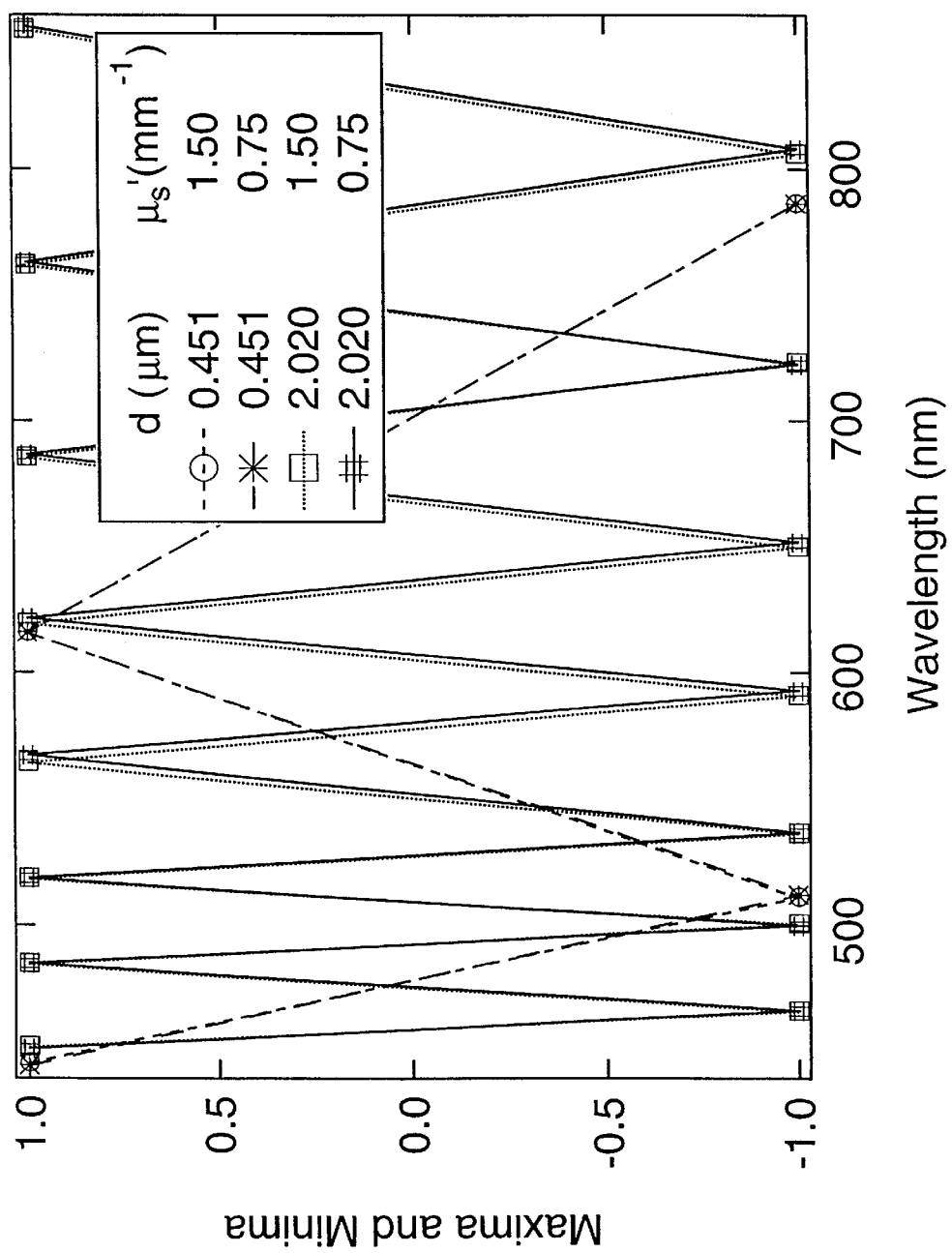
FIG. 5 is a graph of derivatives of the spectra of FIG. 4 in which the maxima were assigned a value of +1 and the minima were assigned a value of −1.

Measurements of Nonabsorbing Tissue Phantoms—Polystyrene Spheres in Water—Effect of Particle Concentration The spectra from four phantoms with particle diameters 0.329, 0.451, 0.890, and 2.020 μm are shown in FIG. 2 and the derivatives of these spectra are shown in FIG. 3. From both figures, it is clear that the spectrum of each size of sphere has a distinct oscillatory pattern. In other words, each pattern is a signature of the size of the particles. The spectra in FIG. 2 were all obtained from suspensions of spheres with $\mu_s'=1.5$ mm$^{-1}$. The same experiments were repeated with a lower reduced scattering coefficient, 0.75 mm$^{-1}$, such that the concentration of the particles is two times lower than in the previous tissue phantoms. As seen in FIG. 4 there is very little difference in the oscillation pattern of spectra from tissue phantoms with the same size polystyrene particles but with two different reduced scattering coefficients, 0.75 mm$^{-1}$ and 1.50 mm$^{-1}$. To see more clearly the variation of the oscillation pattern with wavelength, the maxima and minima of the derivative spectra in FIG. 4 have been assigned values of +1 and −1, respectively. The pattern of the maxima and the minima is the same for the same particle size even for different concentration of the particles as seen in FIG. 5.

EXAMPLE 3

Particle Size Sensitivity

Figure 6:
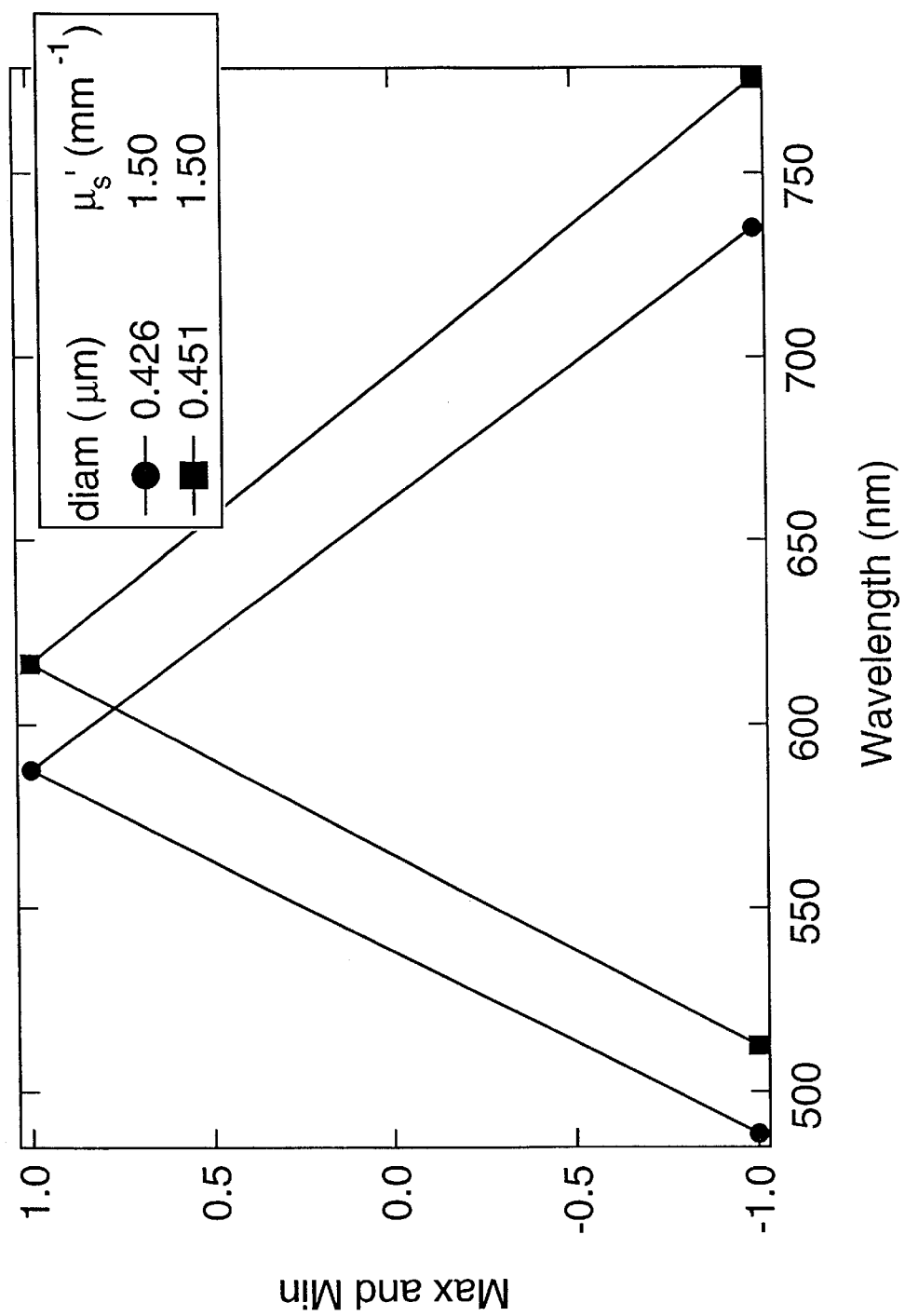
FIG. 6 is a graph of the wavelength positions of the maxima and the minima of the derivatives of the spectra of polystyrene spheres with d=426 and 451 nm.

To test the sensitivity of the technique to scatterer size, two phantoms were prepared using similar size spheres. The diameter of the particles was 0.425 μm (425 nm) in the first phantom and 0.451 μm (451 nm) in the second phantom. The reduced scattering coefficient of both the phantoms was 1.5 mm$^{-1}$. FIG. 6 shows the wavelength positions of the maxima and the minima of the derivatives of the spectra. There is a shift of ~30 nm between the two phantoms.

EXAMPLE 4

Linear Correlation Between Particle Size and Oscillation Frequency

Figure 7:
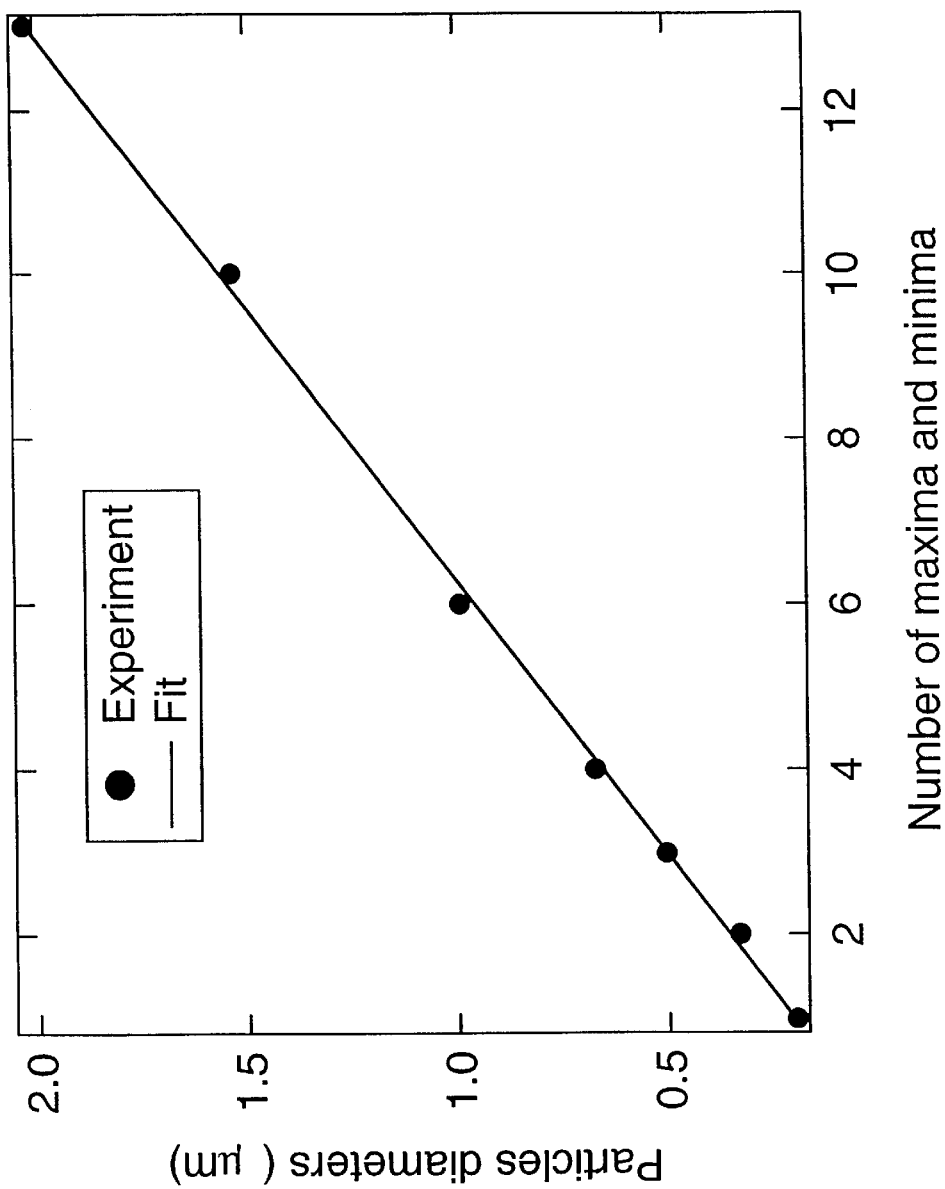
FIG. 7 is a graph of particle diameter as a function of the total number of maxima and minima of the derivatives of the elastic scatter spectrum between 450 and 800 nm.

As seen in FIG. 3, the frequency of oscillations in the derivative spectra increases with particle size. The number of the maxima and minima of the derivatives of the spectra within a specified wavelength range provide information about diameter of the particles. Variation of the size of the particles with the total number of the maxima and the minima in wavelength range 450–800 nm is shown in FIG. 7 for the particles with diameters in the range from 0.107 μm to 2.02 μm. Particle size is approximately a linear function of the total number of maxima and the minima. A linear fit to the experimental data in FIG. 7 has a slope of 0.151 μm. Therefore, increasing the total number of maxima and minima by one corresponds to an increase in particle diameter of 0.151 μm.

EXAMPLE 5

Effects of Changing the Relative Refractive Index

Figure 8:
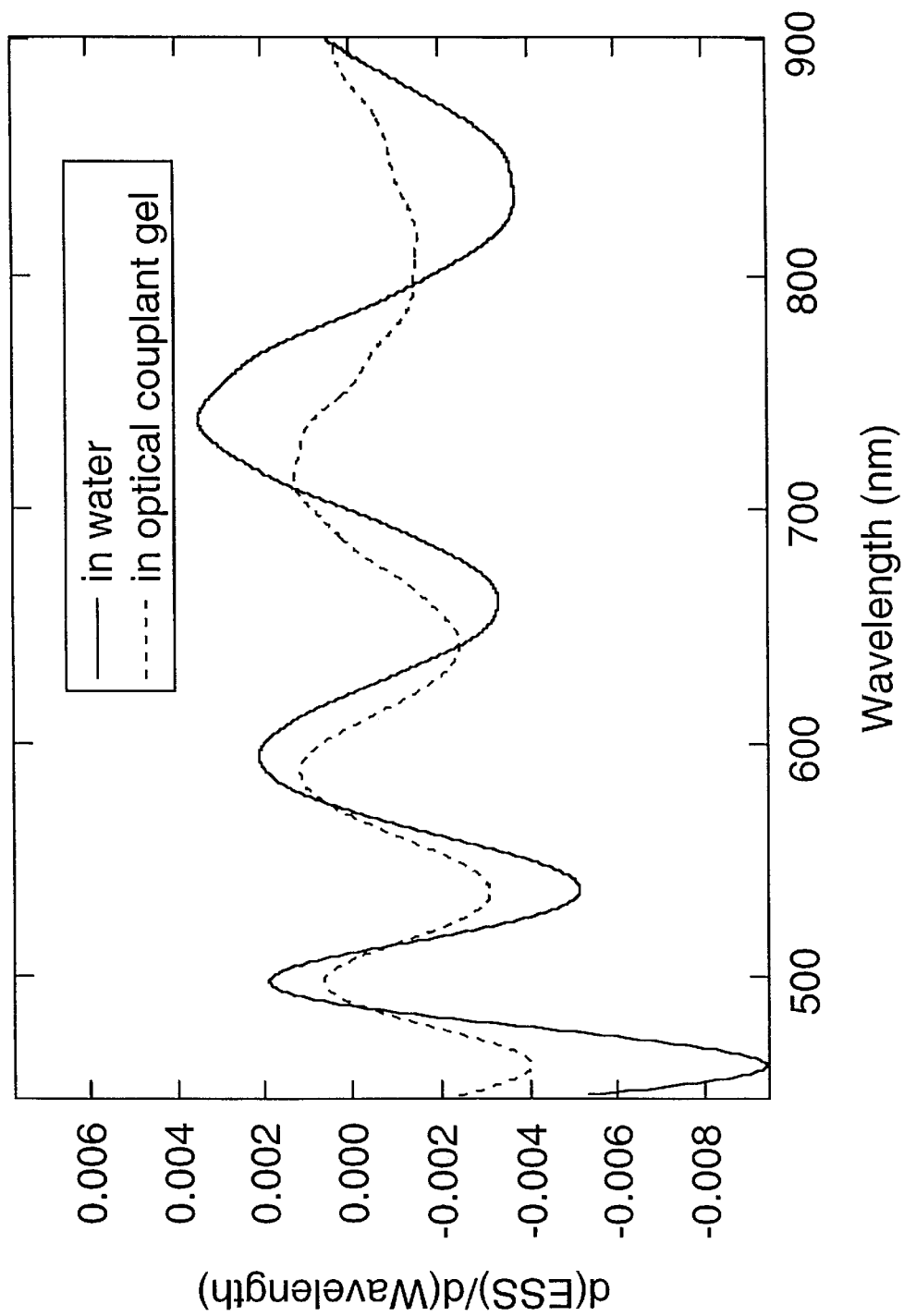
FIG. 8 is a graph of derivatives of the elastic scatter spectra of 0.890 μm diameter polystyrene spheres measured in water and in optical couplant gel, where the reduced scattering coefficient, $\mu_s'=1.5$ mm$^{-1}$.

In some experimental circumstances the refractive indices of the scatterer and the medium may not be exactly known. To experimentally determine the effect of refractive indices, polystyrene spheres of diameter 0.990 μm were immersed in optical couplant (n =1.46) instead of water. As seen in FIG. 8, this large change in the relative refractive indices, 1.20 to 1.09, affected the spacing between adjacent maxima of the oscillations. The distance between adjacent maxima in the derivative spectra decreased by about 10% for the spheres in optical couplant as compared to the spheres in water.

It was postulated that if the change in spacing between maxima is linear with changes in relative refractive index, then a 1% change in refractive index causes a 1% change in spacing. To verify this assumption, two Monte Carlo simulations were run with spherical scatterers of radius 0.2 μm in a medium with an index of 1.33. The index of refraction of the spheres was 1.40 in one simulation and 1.39 in the other. In both cases the density of spheres was such that $\mu_s'=1.5$ mm$^{-1}$ at 633 nm. The position of the maxima and minima was found by fitting second degree polynomials to regions around the maxima and minima. The separation between the maxima and minima was the same for the two simulations to within 1 nm. However, all of the maxima and minima of the simulation of spheres of index 1.39 were shifted 7 nm to the blue of the maxima and mimima of the simulation of spheres of index 1.4.

From the data in FIG. 4, it was estimated that this difference would cause an error of about 8 nm in size determination.

EXAMPLE 6

Effects of Absorption

Figure 9:
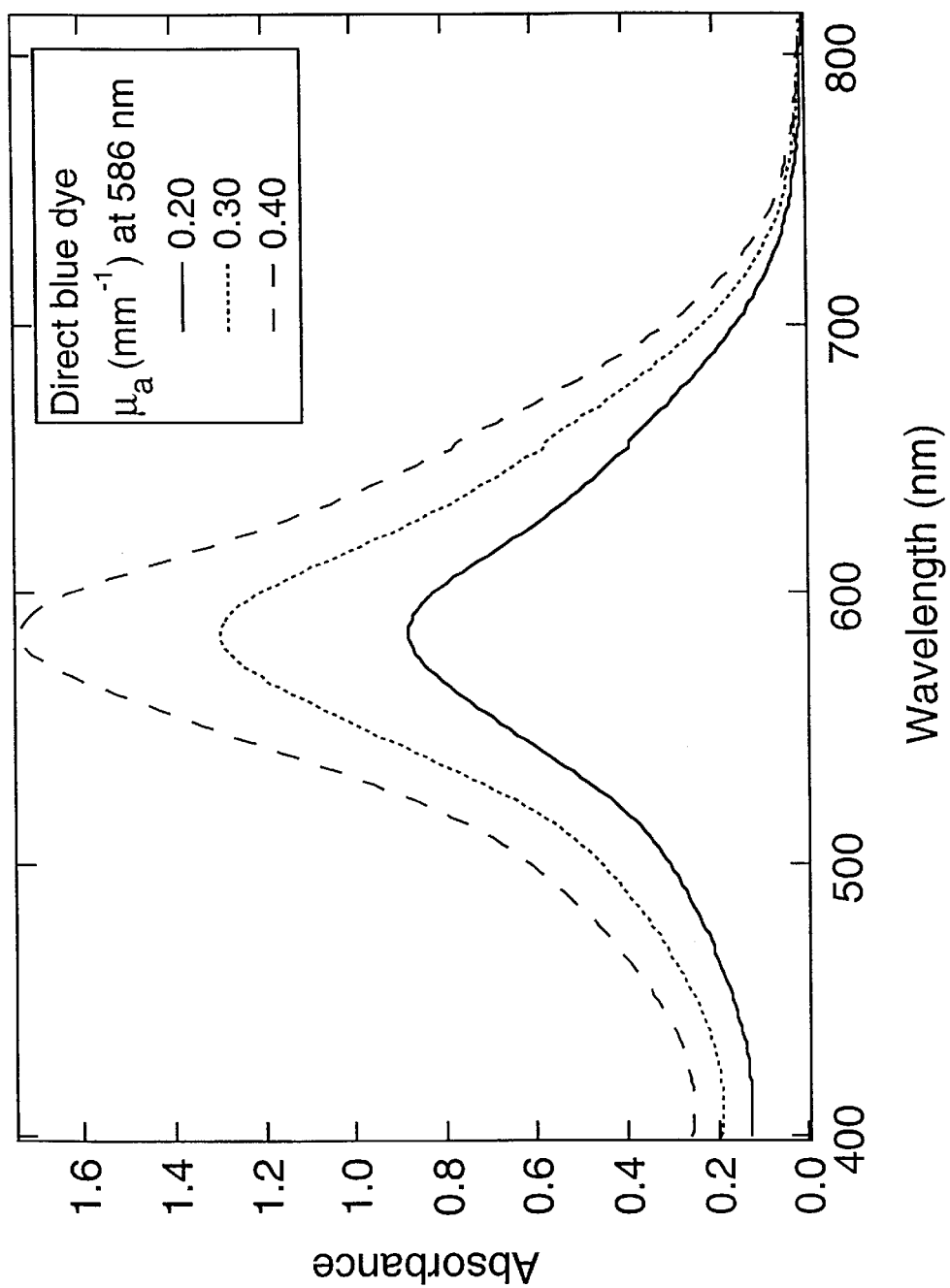
FIG. 9 is a graph of the absorption spectra of blue dye for three different concentrations. Absorption coefficients (absorption divided by log e) at the maxima are 0.20, 0.30, 0.40 mm$^{-1}$.
Figure 10:
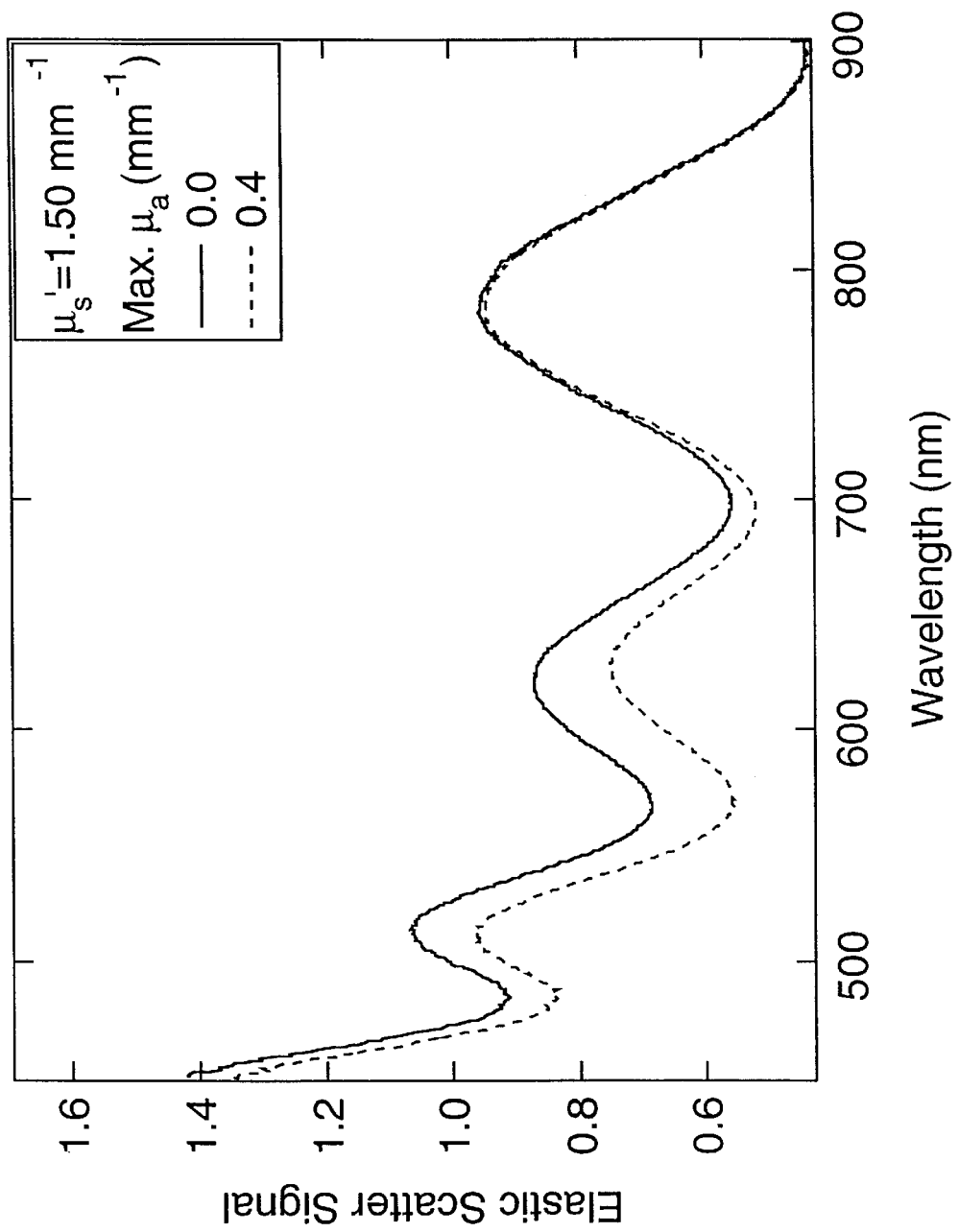
FIG. 10 is a graph of two elastic scatter spectra of 0.990 μm diameter polystyrene spheres, measured before and after adding blue dye. The maximum absorption effect is seen around 600 mn. The reduced scattering coefficient was 1.50 mm$^{-1}$.
Figure 11:
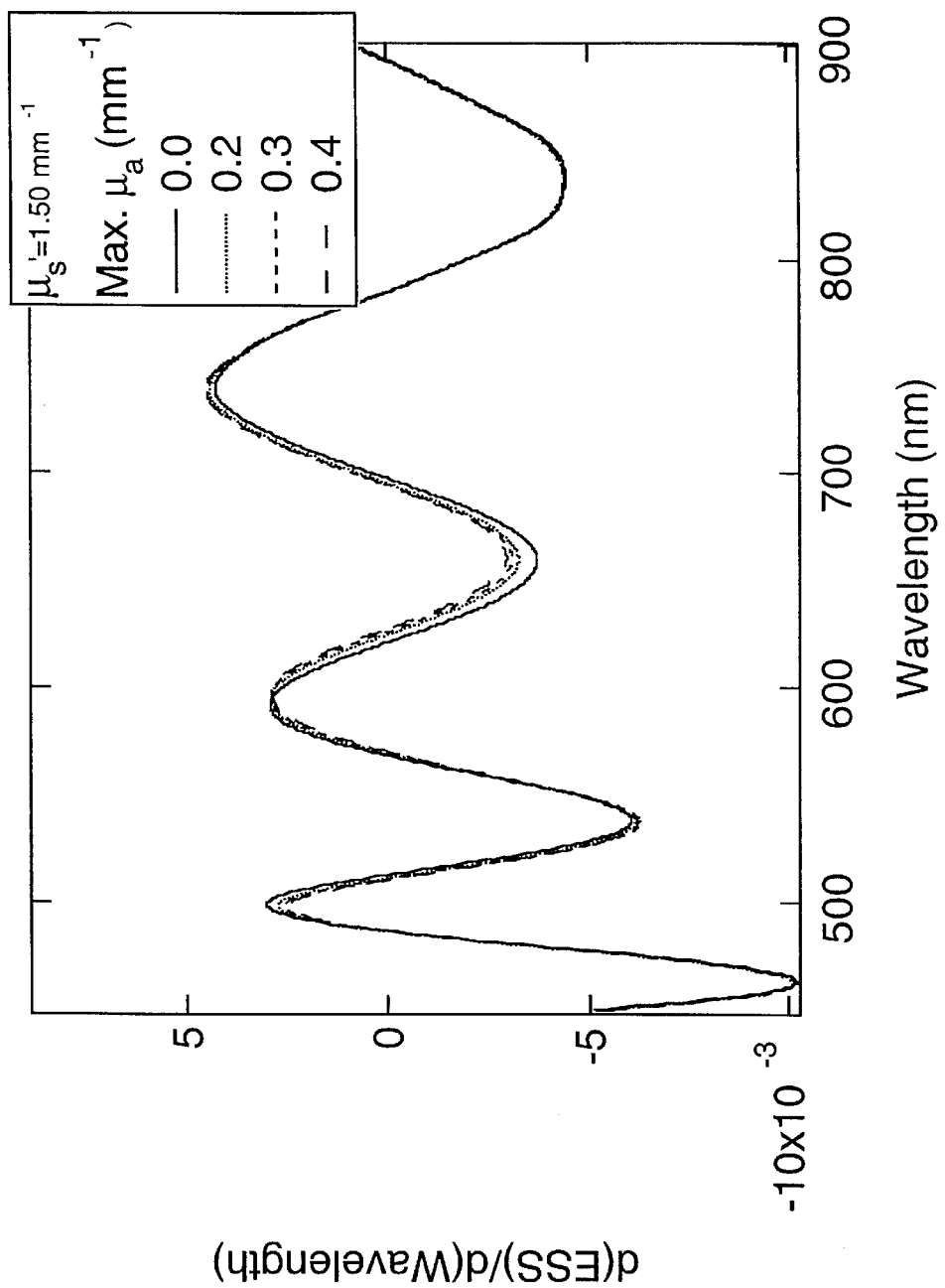
FIG. 11 is a graph of derivatives of one spectrum of 0.990 μm diameter polystyrene spheres before adding blue dye and of three other spectra after adding the dye at different concentrations.

Absorption of light in a turbid media decreases the ESS signal. To determine how absorption affects the determination of particle size, blue dye of three different concentrations was added to three tissue phantoms. The phantoms were prepared with polystyrene particles of diameter 0.990 $\mu$m to have a reduced scattering coefficient of 1.5 mm$^{-1}$. Absorption spectra of blue dye for the three concentrations are seen in FIG. 9, where the maximum absorptions are 0.2, 0.3, and 0.4 mm$^{-1}$ at 586 nm. ESS spectra taken before and after adding blue dye are seen in FIG. 10. The difference between the two spectra is greatest near the maximum absorption of the blue dye. Derivatives of spectra before and after adding blue dye are compared in FIG. 11 for three different blue dye concentrations. The biggest shift of the oscillations is 6.22 nm from 591.49 to 597.71 nm near the wavelength of the maximum absorption for the highest absorption coefficient, 0.4 mm$^{-1}$.

This example demonstrates that a large absorption can have only a small effect on the pattern of maxima and minima in the first derivative of the ESS spectra. The reason that absorption has such a small effect is that the distance a photon travels in the medium is small. Monte Carlo results show that the average pathlength is only 1.4 mm for a suspension of polystyrene spheres of radius 0.5 $\mu$m and $\mu_s$=1.5 mm$^{-1}$. When there is also an absorption of 0.05 mm$^{-1}$, the pathlength decreases to 0.9 mm. From the data in FIG. 10 and knowledge of the absorption, (0.4 mm$^{-1}$ at 585 nm), a pathlength of 0.57 mm was calculated for photons of wavelength 585 nm.

EXAMPLE 7

Accuracy of Monte Carlo Simulations

Figure 12:
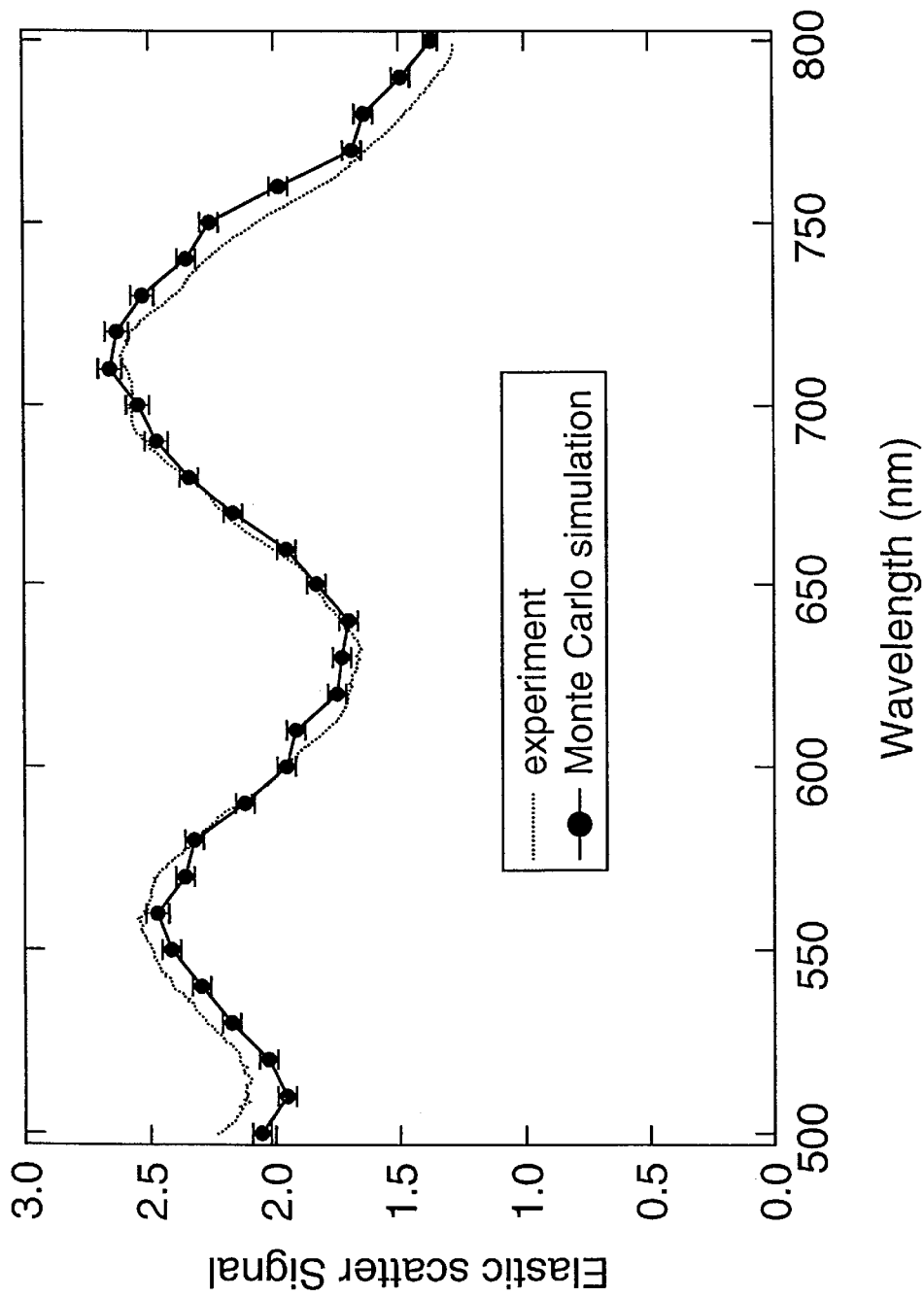
FIG. 12 is a graph comparing experimental measurement and Monte Carlo calculation of the elastic scatter signal for 0.890 μm diameter polystyrene spheres in water with a concentration such that $\mu_s'=1.5$ mm$^{-1}$.

Before using Monte Carlo simulations to examine the effects of a size distribution on oscillations, the Monte Carlo code results were compared to experimental results for monodisperse distributions. The results of a Monte Carlo simulation and experimental measurements of the elastic scatter spectrum of 0.890 $\mu$m diameter polystyrene spheres in water are shown in FIG. 12. There is good agreement of the wavelength dependence of the results.

EXAMPLE 8

Effects of a Distribution of Scatterer Sizes.

Figure 13:
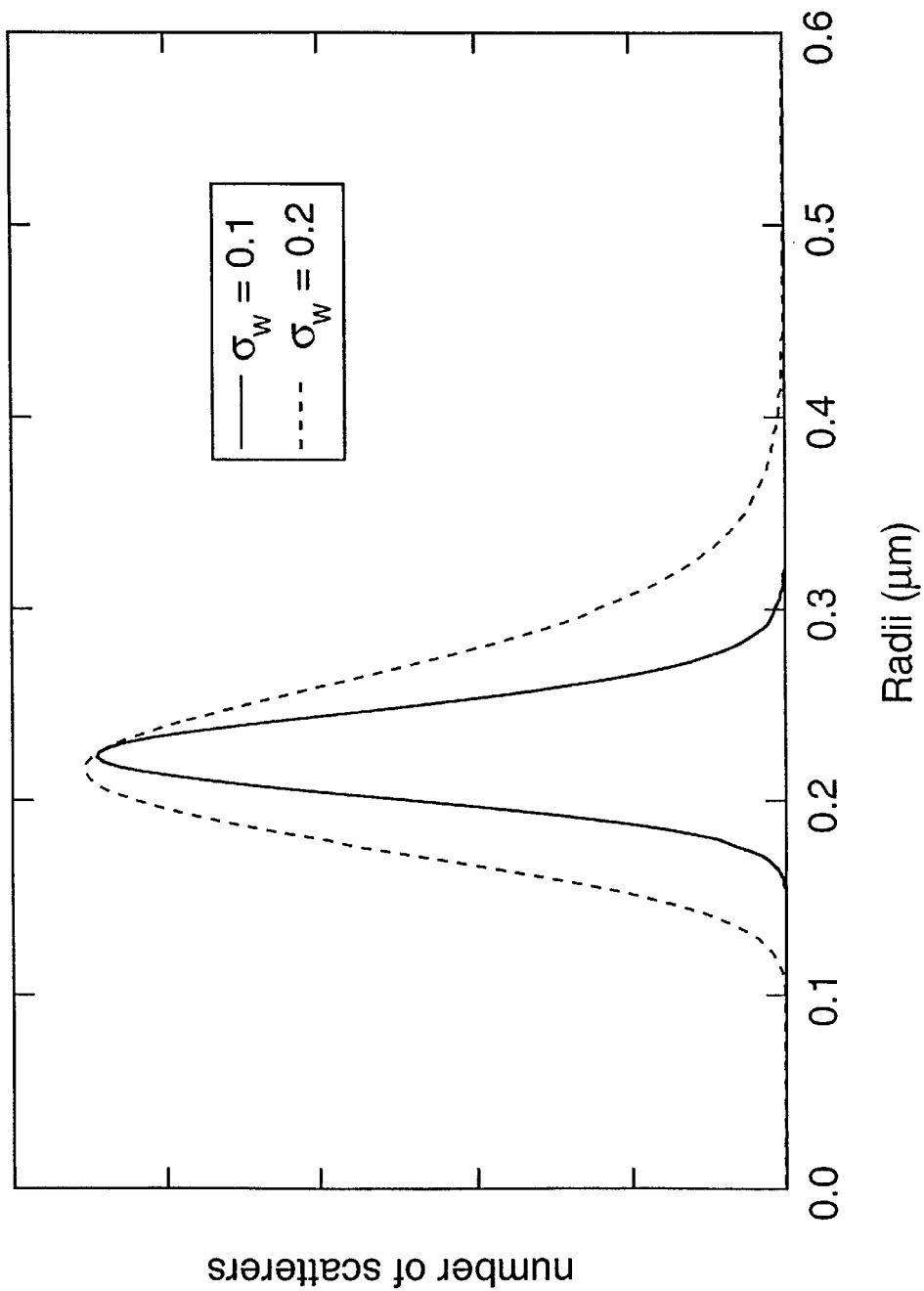
FIG. 13 is a graph of the particle size distributions used in Monte Carlo simulations reported in FIG. 14.

To determine whether the oscillations seen in FIG. 2 as a function of wavelength are still present when there is a distribution of scatterer sizes present, Monte Carlo simulations were performed for several size distributions. For these simulations, an index of refraction of 1.4 for the scatterers and 1.33 for the medium was used to more closely approximate the refractive indices expected in tissue. The distributions used in the simulation are shown in FIG. 13. They were log normal distributions (Eq. 2) with an average scatterer radii of 0.2255 $\mu$m and a width determined by $\sigma_w$=0.1 or 0.2. A log-normal distribution was chosen, because a slightly modified log-normal distribution of spheres has been shown to reproduce the scattering properties of tissue, and it is a common distribution used in particle size analysis. The simulation results are presented in FIG. 14. The oscillations are quite significant for $\sigma_w$=0.1. For $\sigma_w$=0.2 the oscillations are decreased, but still noticeable.

$$f(x)=(1/x)\exp(-(\ln(x)-\ln(x_m))^2/(2(\sigma_w^2))) \quad (2)$$

EXAMPLE 9

Depth Probed in a Single Fiber Experiment

Figure 15:
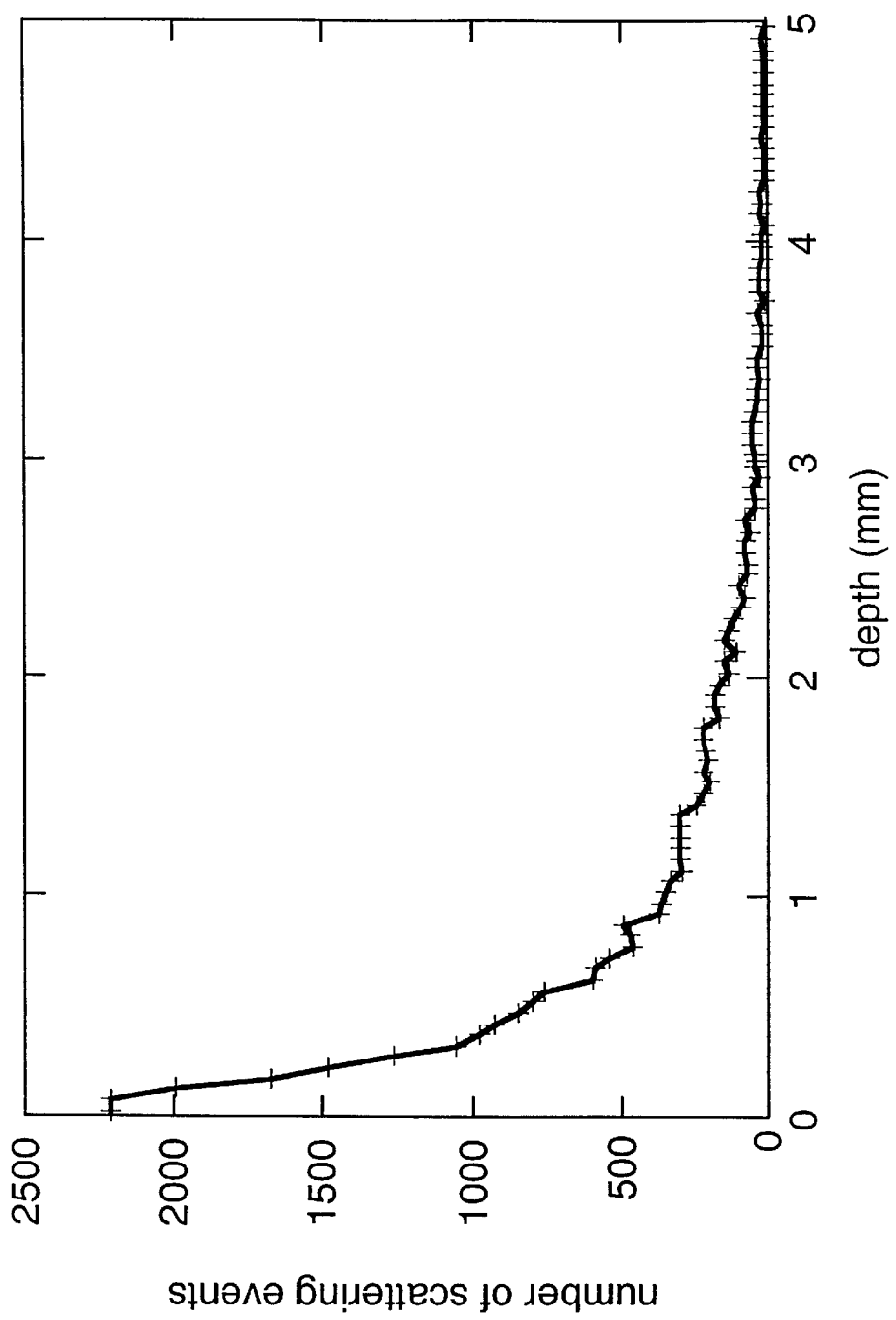
FIG. 15 is a graph of the sum of all scattering events for all collected photons as a function of depth. These results were determined from a Monte Carlo simulation of polystyrene spheres in water: sphere diameter=0.505 μm, g=0.827, $\mu_s'=1.5$ mm$^{-1}$.

Monte Carlo simulations were used to determine the depth of the scattering medium that is interrogated by a single fiber probe. The sum of all of the scattering events as a function of depth for all of the collected photons is plotted in FIG. 15. The optical parameters for this simulation were, g=0.827, $\mu_s'$=1.50 mm$^{-1}$, $\mu_s$=8.663 mm$^{-1}$ and $\mu_a$=0. The probe was 200 $\mu$m in diameter and had a numerical aperture of 0.22. The mean of this distribution was 760 $\mu$m, the mode, i.e. the depth above which half of the scattering events took place, was 420 $\mu$m. Simulations were performed using the same geometry and scattering parameters with absorptions of 0.05, 0.1 and 0.2 mm$^{-1}$. As expected, the depth of photon penetration decreased with increasing absorption. The mean and mode when $\mu_a$=2.0 mm were 296 and 170 $\mu$m, respectively. To assess how a change in the amount of scattering affects the depth of light penetration, $\mu_s$ was reduced by a factor of 2 and the same set of simulations, with $\mu_a$=0 to 0.2 mm$^{-1}$, were run. The penetration depth was similar to the case for $\mu_s$=8.663 mm$^{-1}$ when there was no absorption, mean=760, mode=432 $\mu$m. The reduction in light penetration with increasing $\mu_a$ was not as pronounced, however. For an absorption of 0.2 mm$^{-1}$, the mean and the mode were 400 and 230 $\mu$m, respectively.

EXAMPLE 10

Sensitivity to High Angle Scattering

The amount of light collected using a single fiber for light delivery and light detection is expected to be very sensitive to the probability of backscattering events. To check this hypothesis, a subset of the data from 0.890 $\mu$m spheres was fitted to Equation 3.

$$I(\lambda) = c_0 + c_1\mu_s(\lambda)\int_{\theta_1}^{180°} P(\theta, \lambda)d\theta \quad (3)$$

Figure 16:
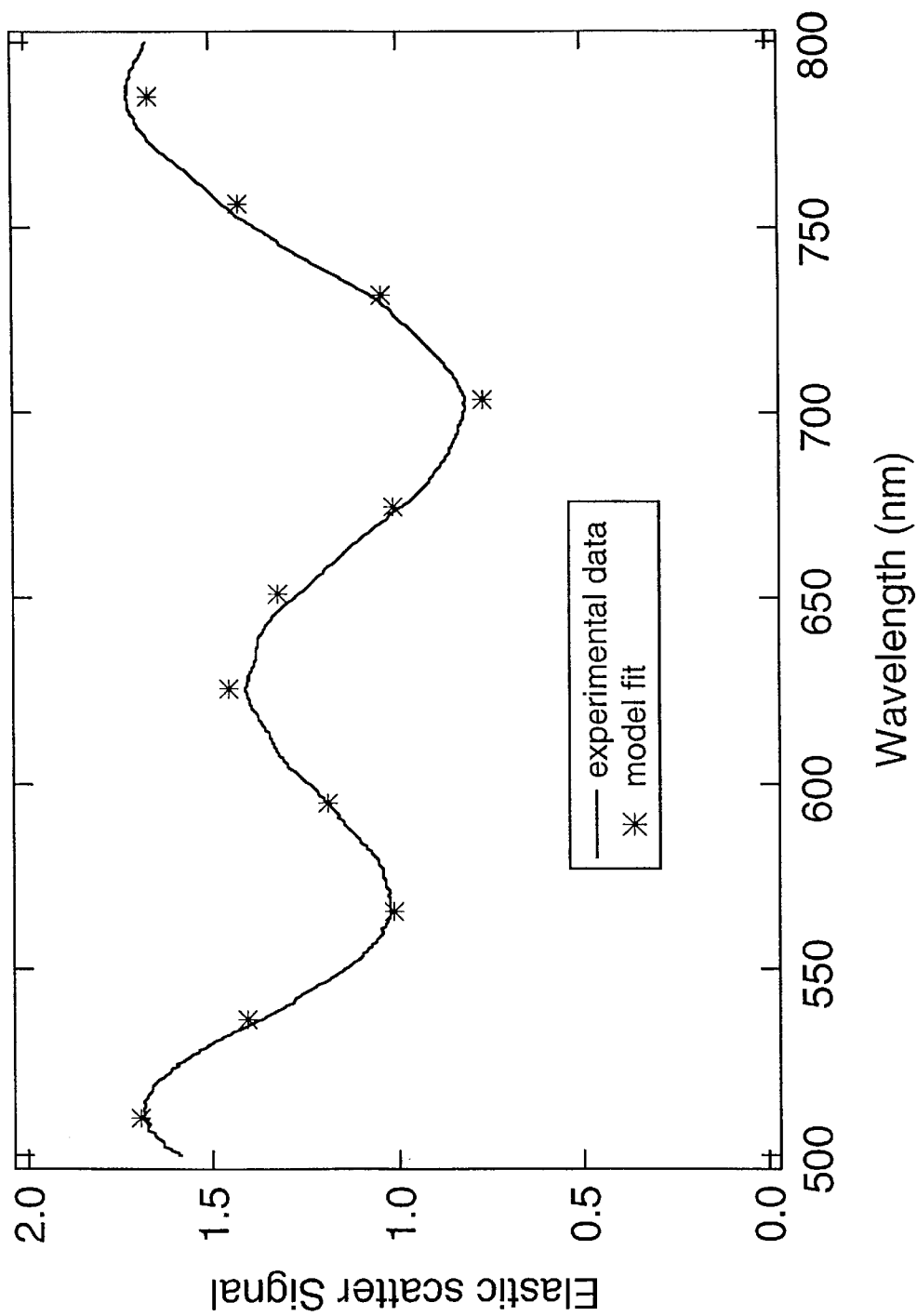
FIG. 16 is a graph of the elastic scatter spectra of 0.990 μm polystyrene spheres and the results of fitting several wavelength points to Equation 2.

The first term in Equation 3 represents light that has been diffusely scattered. The second term represents the backscattered light when $\theta_1$ is large. The parameters resulting from the fit shown in FIG. 16 are, $c_0$=0.5, $c_1$=1.7 and $\theta_1$=147°. The fact that $c_0$ is less than half of the total collected light intensity indicates that diffusely scattered light is not the dominant process. The large value of $\theta_1$ indicates that the wavelength dependent oscillations are due to the wavelength dependence of the probability of high angle scattering events. The first term in Equation 3 could be slightly wavelength dependent because $\mu_s'$, which characterizes the diffusely scattered light, is wavelength dependent. Adding a linear wavelength dependence had only a small affect on the results, $\theta_1$ changed by <2%.

When the scattering medium consists of a monodisperse distribution of spheres of known refractive index, the scatterer size can be approximately determined by examining the number of maxima and minima between 450 and 800 nm. To obtain an accuracy better than 0.15 $\mu$m, a comparison of the pattern of maxima and minima to a library of maxima and minima for different size spheres will be needed. These techniques for determining scatterer size will work for a variety of scatterer sizes (~0.1 to 2 μm) and scatterer densities corresponding to reduced scattering coefficients in the range of about 0.75 to 1.5 mm$^{-1}$. As demonstrated in FIG. 4, the pattern of maxima and minima does not depend on scatterer density. It was also observed that the single fiber measurements are insensitive to whether the scatterers are dissolved in a liquid or a solid. In contrast, some particle sizing techniques such as dynamic light scattering require that the scatterers be immersed in a liquid. Thus, the techniques described herein can be adapted to a variety of non-liquid applications, including in-vivo tissue analysis and powder analysis for drug tablets.

If the oscillation pattern is to be used for particle size determination in situations where the exact index of the scatterer or medium is not known, small errors in the size determination will occur. These errors will be small if the estimated refractive indices are close to the actual refractive indices. The presence of absorption may also cause inaccuracies in the estimation of particle size. Absorption causes a decrease in the ESS signal that depends on the pathlength of the collected photons. When the pathlength is longer more light is absorbed. The shortest pathlengths for a given scattering media are obtained when a single fiber is used for both light delivery and light collection. The results of Example 6 demonstrate that because the pathlength traveled in the medium is relatively short, a fairly large absorption is needed to effect the position of maxima and minima. The maximum absorption in FIG. 9 is larger than the hemoglobin absorption in tissue in the green region of the spectrum. The width of the absorption band also determines whether it will effect measurement of the oscillation pattern. If the absorption is narrower than the separation between adjacent minima, it may cause a false minimum. Narrow absorption bands are most likely to cause problems in measurement of the size of the small particles due to the greater separation of adjacent maxima for small particles.

Figure 14:
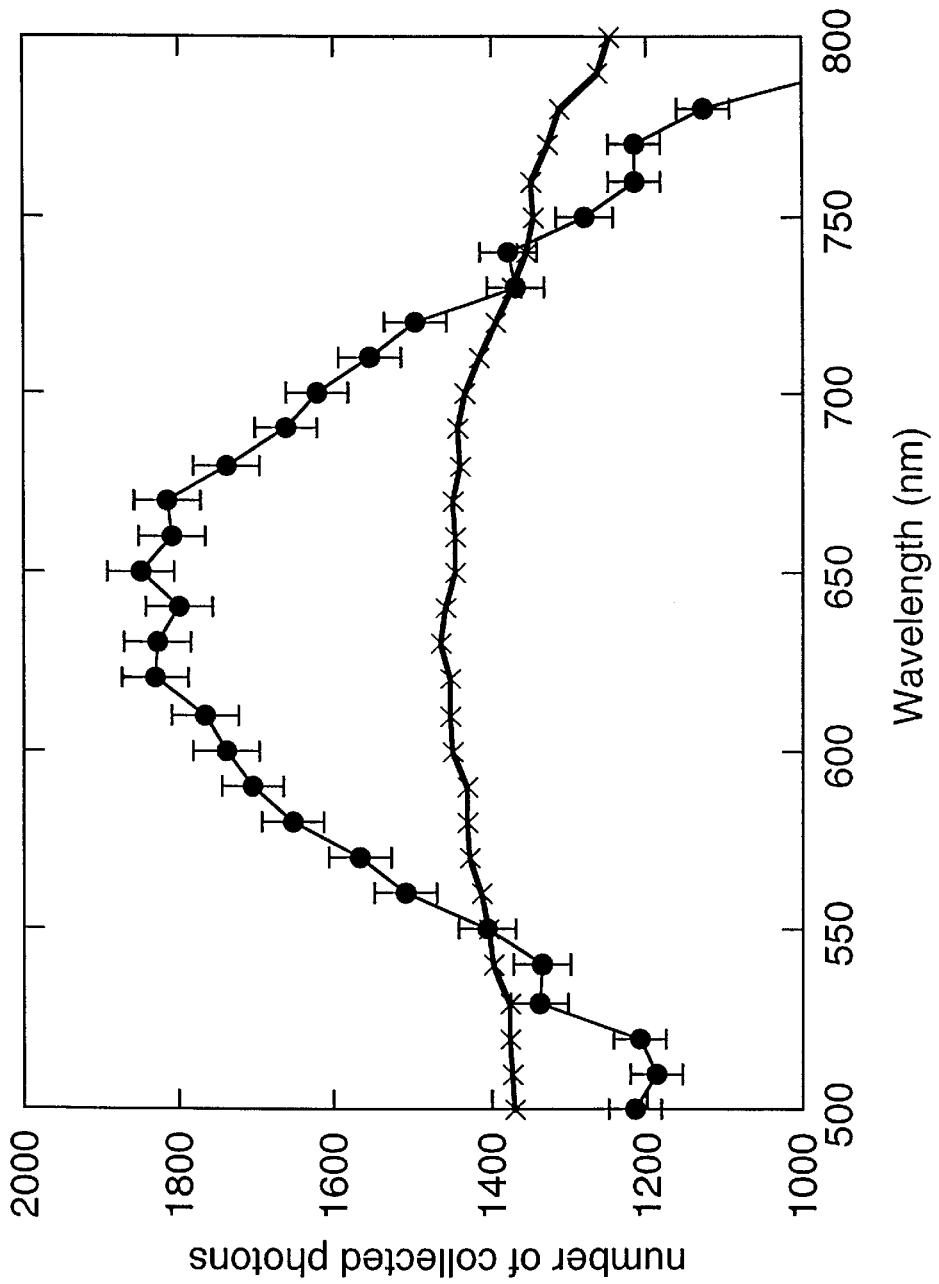
FIG. 14 is a graph of the number of collected photons as a function of wavelength for the size distributions in FIG. 13. The circles are the results of the narrower size distribution in FIG. 13, while the crosses are the results for the broader size distribution. The error bars are the square root of the number of collected photons. The results for the larger size distribution were smoothed with a 5-point box car moving average.

FIGS. 13 and 14 demonstrate that the oscillations as a function of wavelength do not disappear until the scatterer size distribution is reasonably large. This information may be used to determine both scatterer size and the width of the size distribution. An analytical inversion method is not possible at this time, because there is not an analytical expression for the dependence of the ESS signal on particle size distribution. At the moment, the only possible methods for solving the inverse problem are to use a library of wavelength dependent Monte Carlo results or iteratively perform forward Monte Carlo problem while changing the mean and width of the size distribution to minimize Chi-squared.

Regardless of whether measurement with a single optical fiber can be used to easily quantify scatterer size in tissue, the use of a single optical fiber rather than separate delivery and collection fibers has some advantages for measuring scattering properties. The major advantage is the decreased depth of light penetration. Most cancers originate in epithelial tissue, which is only a few hundred microns thick. Consequently, it is desirable for most of the scattering events of the collected photons to take place within 500 μm of the surface as is the case in a single fiber measurement. A second advantage of a single fiber is the reduced interference of absorption in the measurement of scattering properties. Finally, measurements with a single fiber are more sensitive to back scattering. This high-angle scattering is most likely due to the smaller particles. Therefore, a single fiber measurement may be more sensitive to changes in the nuclear structure/morphology of cells. Intranuclear morphology/structure is known to change with malignant progression.

From the foregoing it will be appreciated that the present invention provides an in situ method and apparatus to detect scatterer size and alterations of scatterer size in tissue, turbid, or dense media.

The present invention may be embodied in other specific forms without departing from its essential characteristics. The described embodiments are to be considered in all respects only as illustrative and not restrictive. The scope of the invention is, therefore, indicated by the appended claims rather than by the foregoing description.

What is claimed and desired to be secured by United States Letters Patent is:

1. A method of measuring scatterer size in a turbid medium comprising the steps of:
   obtaining an optical probe comprising a single optical fiber that is optically coupled to a light source and optically coupled to a spectrograph;
   introducing light from the light source to the optical probe such that the light passes from the optical probe to a sample of the turbid medium;
   collecting light scattered by the turbid medium with the optical probe and transmitting said collected light from the optical probe to the spectrograph;
   measuring the collected light with the spectrograph to determine an elastic scatter signal spectrum of the turbid medium;
   counting the number of oscillations in the elastic scatter signal spectrum; and determining the scatterer size as a function of the number of oscillations.

2. The method of claim 1, wherein the optical probe has a diameter in the range from 50 μm to 600 μm.

3. The method of claim 1, wherein the optical probe has a diameter in the range from 100 μm to 300 μm.

4. The method of claim 1, wherein the optical probe has a numerical aperture less than 0.3.

5. The method of claim 1, wherein the optical probe has a numerical aperture less than 0.22.

6. The method of claim 1, wherein the optical probe comprises a tip structurally modified to inhibit specular reflection of the light.

7. The method of claim 1, wherein the optical probe comprises a tip polished at an angle sufficient to inhibit specular reflection of the light.

8. The method of claim 1, wherein optical probe comprises a tip polished at an angle in the range from 45 to 55 degrees.

9. The method of claim 1, wherein the optical probe is constructed of one or more quartz fibers.

10. The method of claim 1, wherein the turbid media spectra is measured in the wavelength range from 100 to 900 nm.

11. The method of claim 1, further comprising the steps of determining the refractive index of the medium and adjusting the representation of the scatterer size to compensate for the refractive index of the medium.

12. The method of claim 1, wherein the turbid media spectra is measured in the wavelength range of 450 to 800 nm.

13. A method of measuring particle size of a scatterer in a turbid medium comprising the steps of:
   obtaining an elastic scatter signal spectrum of the turbid medium;
   counting the number of oscillations in the elastic scatter signal spectrum of the turbid medium within a predetermined wavelength range; and
   determining the scatterer size as a function of the number of oscillations.

14. The method of claim 13, wherein the predetermined wavelength range is from 450 to 800 nm.

15. The method of claim 13, wherein the elastic scatter signal spectrum is obtained by the steps of:
   introducing light into a sample of the turbid medium;
   collecting light scattered by the turbid medium with an optical probe;
   transmitting said collected light from the optical probe to a spectrograph; and
   measuring the collected light with the spectrograph to determine an elastic scatter signal spectrum of the turbid medium.

16. The method of claim 15, wherein the optical probe is optically coupled to a light source and optically coupled to the spectrograph, such that the optical probe introduces light into the sample and collects light scattered by the turbid medium.

17. The method of claim 15, wherein the optical probe has a diameter in the range from 50 $\mu$m to 600 $\mu$m.

18. The method of claim 15, wherein the optical probe has a diameter in the range from 100 $\mu$m to 300 $\mu$m.

19. The method of claim 15, wherein the optical probe has a numerical aperture less than 0.3.

20. The method of claim 15, wherein the optical probe has a numerical aperture less than 0.22.

21. The method of claim 15, wherein the optical probe comprises a tip structurally modified to inhibit specular reflection of the light.

22. The method of claim 15, wherein the optical probe comprises a tip polished at an angle sufficient to inhibit specular reflection of the light.

23. The method of claim 15, wherein optical probe comprises a tip polished at an angle in the range from 45 to 55 degrees.

* * * * *